United States Patent [19]

Wess

[11] Patent Number: 4,570,634

[45] Date of Patent: Feb. 18, 1986

[54] SHOCKWAVE REFLECTOR

[75] Inventor: Othmar Wess, Immenstaad, Fed. Rep. of Germany

[73] Assignee: Dornier System GmbH, Friedrichshafen, Fed. Rep. of Germany

[21] Appl. No.: 545,203

[22] Filed: Oct. 25, 1983

[30] Foreign Application Priority Data

Nov. 6, 1982 [DE] Fed. Rep. of Germany ....... 3241026

[51] Int. Cl.[4] ............................................ A61B 17/22

[52] U.S. Cl. .................................... 128/328; 367/138

[58] Field of Search ..................... 128/660, 24 A, 328; 367/138, 151, 166, 171, 902

[56] References Cited

U.S. PATENT DOCUMENTS 3,942,531 3/1976 Hoff et al. ........................... 128/328

4,311,147 1/1982 Häusler ............................... 128/328

*Primary Examiner*—V. Millin

*Assistant Examiner*—Gregory Beaucage

*Attorney, Agent, or Firm*—Ralf H. Siegemund

[57] ABSTRACT

A reflector for focusing shockwaves in order to contactlessly comminute concretions in living bodies and for which a suitable selection of materials and geometry prevents a transverse wave in the reflector material from leading the shockwave front in the coupling medium.

5 Claims, 1 Drawing Figure

SHOCKWAVE REFLECTOR

Figure 1:
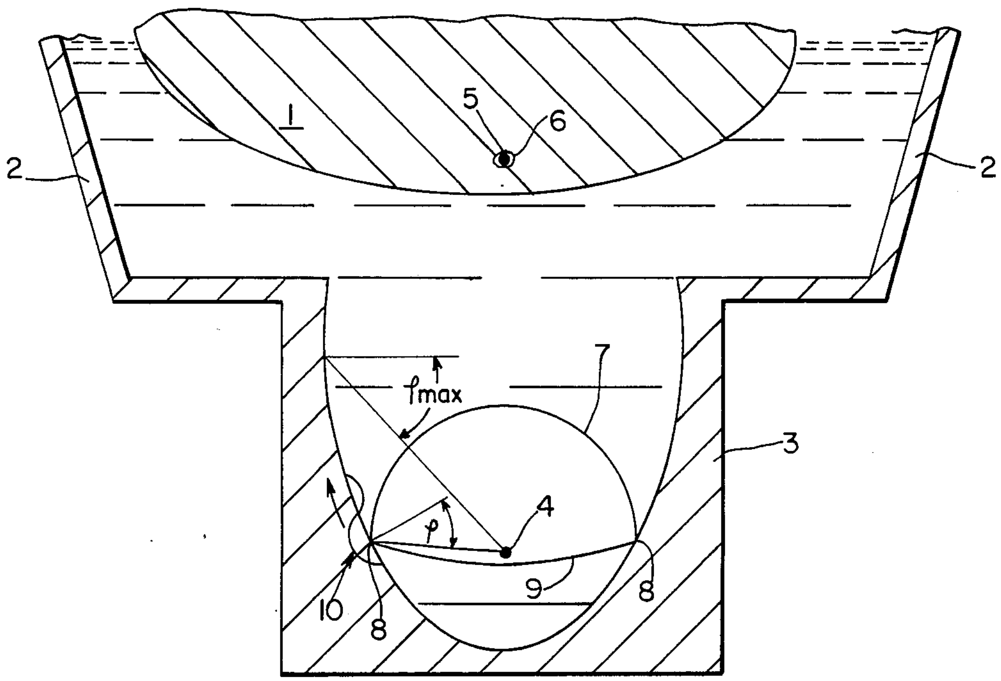

This invention relates to a shockwave reflector for the contactless comminution of concretions in living bodies.

The reflector is in the shape of an ellipsoid and the purpose thereof is to focus shockwaves generated in a spark gap in the first focus and spreading through a liquid in the reflector toward the second focus where the concretion, for instance a kidney stone to be destroyed, is located. The reflector must transmit as high a proportion as possible of in-phase energy generated in the first focus to the second focus.

Brass reflectors with an encompassing angle of about 250° are known, wherein the full solid angle ($4\pi$) is utilized to about 90% and where the ratio of the axes a : b is about 2 : 1 (E. Schmiedt: Beitraege zur Urologie, [Contributions to Urology], Volume 2, pp. 8–13, Munich 1980). The material is selected on the basis of the maximum possible step in acoustic impedence $z = \rho.c$ (where $\rho$=density, c =speed of sound) between the liquid and the reflector material in order to achieve a high coefficient of reflection. Further, boundary conditions such as stability and easy working to-date have led to the use of brass.

It is the object of the present invention to provide a reflector which focuses shockwaves more efficiently than the reflectors heretofore known.

The invention is based on the concept that the step in acoustic impedance $\rho.c$ is not the only determining value for good focusing, rather that the speeds of the acoustic wave in the reflector material and in the liquid must be matched. The waves impinging on the reflector surface produce, among other effects, transverse vibrations in the reflector which spread in the reflector material and the surface thereof with characteristic speeds of propagation. Interferences occur in the reflected wavefront when the reflection surface vibrates in a direction normal to the surface because of differences in travel times as the primary wave front impinges.

In-phase focusing on the second focus is achieved when the wave propagates faster in the liquid than in the reflector. In that case, the wavefront always impinges on a reflector surface at rest.

However, the invention also permits the use of materials of which the transverse surface speed exceeds the speed of sound in the coupling medium, for instance water, provided the advance of the surface wave is prevented by the geometry of the reflector by observing certain conditions. The reflected operative wave then remains itself unaffected and retains the original steepness of slope of the primary wave. All other interferences, for instance those produced by the lagging surface wave, are delayed in time behind the operative wave and cannot impair the focusing procedure.

The reflectors of the invention achieve a substantially better focusing than heretofore because all wave portions are superposed in phase; the steepness of the slope of the pressure increase—which is essential for comminution—remains high. The comminution output increases, fewer applications than heretofore are required, thereby relieving the patient of stress and increasing the service life of the spark gap even more.

The invention will be further illustrated by reference to the accompanying drawings in which:

FIG. 1 is a schematic view in cross-section of a shockwave reflector in accordance with the present invention.

In schematic form, FIG. 1 shows a human body 1 with a kidney stone 6, in a water-filled tub 2. An ellipsoidal reflector 3 with the two foci 4 and 5 is mounted at the lower side of the tub 2 and is also filled with water. A spark gap (not shown) is positioned at the focus 4 inside the reflector 3 and generates shockwaves by submerged discharges. The concretion to be destroyed, for instance the kidney stone 6, is located at the second focus 5 outside the reflector. The limit angle $\rho_{max}$ is defined by the reflector geometry. When a submerged discharge is ignited at the focus 4, a shockwave front 7 spreading spherically is generated and is transmitted by the reflector 3 as a reflected shockwave front 9 to the kidney stone. Parts of the kidney stone are made to shatter due to the high amplitudes of compression and tension. FIG. 1 shows the shockwave front 7 which has just arrived at the points 8 of the reflector surface. The instantaneous angle of incidence thereof on the reflector surface is $\rho$. For the most part, the incident shockwave front 7 is reflected (front 9), but it also produces a transverse surface wave 10 (not shown to scale) which spreads in the reflector surface (arrow). When the material and the geometry are selected in accordance with the invention, the primary wave 7 moves more rapidly over the reflector surface than does the interfering transverse wave 10. The primary wave 7 therefore will always be incident on a surface material at rest and is reflected without interference. The reflected wave front 9 retains the original steepness of slope of the pressure increase. All reflected portions superpose in phase, and hardly any energy is lost in comminuting the stone 6. When the conditions of the invention are not observed, the primary wave 7 will be incident on parts of the reflector which already were excited by the surface wave 10. Due to the interaction of the primary wave 7 with the surface wave 10, the reflected wave 9 then will be impaired by interference in amplitude and phase. Consequently, energy for concretion comminution will be lacking or the pressure increase at the site of the concretion takes place too slowly because of out-of-phase superposition of the individual portions.

The invention will be further illustrated by reference to the following specific examples:

EXAMPLE 1

The condition $c_{TO} < c_S$ is met when lead is used as the reflector material and water as the coupling liquid. The transverse speed of sound $C_{TO}$ in lead is 710 m/s and hence much less than the speed of sound $c_S$ in eater of 1,480 m/s, and, accordingly, the spreading primary wave 7 is always faster than the surface wave 10. The above condition therefore is always met regardless of the reflector geometry. No critical angle $\rho_K$ occurs. There is no need to make the entire reflector body of lead. It is sufficient that the interior reflector surface be lead-covered.

EXAMPLE 2

The condition of the invention also can be met with reflectors made of a material where $c_{TO} > c_S$. A water-filled reflector made of tin ($c_{TO}$=1,670 m/s) with semi-axes a =12.5 cm and b =7.5 cm meets the condition of the invention provided the maximum angle of incidence $\rho_{max}$ is less than the critical angle $\rho_K$ =62.4°.

EXAMPLE 3

For a brass reflector of the state of the art ($c_{TO}=2,120$ m/s), when filled with water, the critical angle is 44.8° but the maximum angle of incidence is 53.1°. It does not meet the condition of the invention, and no optimum focusing exists. For the same material, focusing can be improved by selecting the ratio of the ellipsoid axes closer to unity or by relinguishing the boundary zones (lesser enclosure angles). However, the boundary zones are exceedingly important for transmission and should be retained.

Similarly to the sonic barrier, the situation arises for the critical angle $\rho_K$ that the source of the surface oscillation (the incident primary front) spreads on the reflector surface at the speed of propagation $c_{TO}$ of the surface wave itself and therefore couples in-phase energy into the surface wave. Only after $\rho$ has enlarged after a certain path jointly covered and due to the altered reflector geometry will it be possible for the presently high energy surface wave of the incident shockwave front to become leading and to radiate the energy thereof in the form of a Mach cone (modified by the curved reflector surface) and also to partially deliver it ahead of the actual operative wave to the focusing area.

It will be obvious to those skilled in the art that many modifications may be made within the scope of the present invention without departing from the spirit thereof, and the invention includes all such modifications.

What I claim is:

1. In a reflector for focusing, shockwaves in a coupling liquid in order to contactlessly comminute concretions in living bodies,
   the improvement comprising interior reflecting surface means in which the speed of propagation $c_{TO}$ of a transverse surface wave in said reflecting surface means is less than the speed of sound $c_S$ in the coupling liquid filling the reflector.

2. A reflector according to claim 1, in which the coupling liquid is water and the interior reflecting surface means is lead, tin or tantalum.

3. In a reflector for focusing shockwaves in a coupling liquid in order to contactlessly comminute concretions in living bodies,
   the improvement comprising that the interior geometry of the reflector and the reflecting material of the interior reflector surface are in accordance with the following equation:

$$\rho_{max} > \rho_K = \text{arcsine } c_S/c_{TO}$$

wherein $\rho_{max}$ = maximum possible angle of incidence, $\rho_K$ = critical angle, $c_S$ = speed of propagation of the shockwave inside the reflector, and $c_{TO}$ = speed of propagation of the transverse surface wave in said reflecting material.

4. A reflector according to claim 3, in which the reflector is a partial ellipsoid of which the limit angle $\rho_{max}$ is less than the angle $\rho_K$ because of a smaller enclosing angle.

5. A reflector according to claim 3, in which the ratio of the axes a:b of the reflector body is near to unity.

* * * * *